(12) United States Patent
Haroun et al.

(10) Patent No.: US 11,891,390 B1
(45) Date of Patent: Feb. 6, 2024

(54) 3-SUBSTITUTED AMINO-2-ARYLPYRROLO[2,3-C]PYRIDINES AS CK2 INHIBITORS

(71) Applicant: KING FAISAL UNIVERSITY, Al-Ahsa (SA)

(72) Inventors: Michelyne Haroun, Al-Ahsa (SA); Christophe Tratrat, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/239,940

(22) Filed: Aug. 30, 2023

(51) Int. Cl.
*A61K 31/437* (2006.01)
*C07D 471/04* (2006.01)
*A61P 35/00* (2006.01)

(52) U.S. Cl.
CPC ............ *C07D 471/04* (2013.01); *A61P 35/00* (2018.01)

(58) Field of Classification Search
CPC .......................... A61K 31/437; C07D 471/04
USPC .......................................... 514/300; 546/113
See application file for complete search history.

(56) References Cited

PUBLICATIONS

Jordan, V. C. Nature Reviews: Drug Discovery, 2, 2003, 205.*
Vippagunta, et al. Advanced Drug Delivery Reviews, 48, 2001, 18.*
Hooper, et al., "Preparation and Antibacterial Activity of Isatogens and Related Compounds", Journal of Pharmacy and Pharmacology, vol. 17, Issue 11, Nov. 1965, pp. 734-741.

* cited by examiner

*Primary Examiner* — Douglas M Willis
(74) *Attorney, Agent, or Firm* — Nath, Goldberg & Meyer; Richard C. Litman

(57) ABSTRACT

Pyrrolo[2,3-c][2,7]naphthyridine-2-carboxylic acid compounds are provided. The pyrrolo[2,3-c][2,7]naphthyridine-2-carboxylic acid compounds have the general formula:

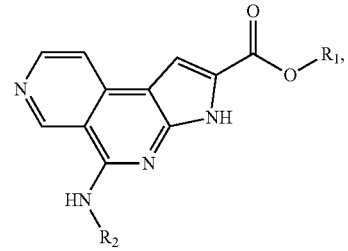

where $R_1$ is H, $C_1$-$C_6$ alkyl, or $C_3$-$C_6$ cycloalkyl, and $R_2$ is $C_1$-$C_6$ alkyl, $C_1$-$C_6$ haloalkyl, $C_1$-$C_6$ cyanoalkyl, $(CH_2)_{2-3}NR_3R_4$, $(CH_2)_{1-2}$aryl, $(CH_2)_{1-2}$heteroaryl, $C(O)$—$(CH_2)_{2-3}NR_3R_4$, $C(O)$aryl, $C(O)$heteroaryl, $S(O)_2$—$(CH_2)_{2-3}NR_3R_4$, $S(O)_2$aryl, $S(O)_2$heteroaryl, $C_3$-$C_6$ cycloalkyl, $C_3$-$C_6$ halocycloalkyl, $C_3$-$C_6$ cyanocycloalkyl, aryl, or 5- or 6-membered heteroaryl. The pyrrolo[2,3-c[2,7]naphthyridine-2-carboxylic acid compounds inhibit protein kinase CK2 activity and may be used as anticancer agents, as well as agents for treating inflammation, pain, immunological disorders, diabetes, viral infections, and neurodegenerative diseases.

12 Claims, No Drawings

3-SUBSTITUTED AMINO-2-ARYLPYRROLO[2,3-C]PYRIDINES AS CK2 INHIBITORS

BACKGROUND

1. Field

The present disclosure provides novel 3-substituted amino-2-arylpyrrolo[2,3-c]pyridine compounds that inhibit protein kinase CK2 activity, compositions containing such compounds and method of preparation. These compounds and compositions are useful as therapeutic agents for treating proliferative disorders such as cancer, as well as other kinase-associated conditions including inflammation, pain, and certain immunological disorders, and other types of diseases such as diabetes, viral infection, and neurodegenerative diseases.

2. Description of the Related Art

The implication of the protein kinase CK2 in various cellular processes such as cell growth, proliferation, death and differentiation constitute a promising drug target for cancer therapy. The overexpression of protein kinase CK2 was reported in multiple cancer types. Recent evidence suggests that CK2 also acts as a suppressor of apoptosis by phosphorylating pro-apoptotic proteins. To date, only one CK2 inhibitor CX-4945 sold under the name of Silmitasertib, an orally active drug developed by Cylene Pharmaceuticals, is currently in clinical use for the treatment of advanced solid tumors (breast, ovarian, etc.) and multiple myeloma. The astonishing pharmacological profile of the anti-cancer drug, Silmitasertib, opens the door for the development of novel potent and selective CK2 inhibitors for cancer chemotherapy.

Multiple series of CK2 inhibitors have been studied for their activities in inhibiting cell growth alone as well as in combination with other anti-proliferation agents (U.S. Pat. Nos. 9,062,043B2, 7,956,064B2; publication WO 2010080170 A1 and WO 2011011199 A1). Combining CK2 inhibitors with an anti-cancer agent that prohibits cell growth such as alkylating agents, anti-metabolite, vinca alkaloid, taxane, topoisomerase inhibitors, anti-tumor antibiotics, and tyrosine kinase inhibitors to treat or ameliorate a neoplastic disorder has been disclosed in WO 2010080170 A1. Additionally, WO 2010008170 A1 also discloses combining CK2 inhibitors with immunosuppressive macrolide to treat a neoplastic disorder.

Certain CK2 inhibitors are also shown to combine with inhibitors to molecules that are essential in cell growth pathway such as AKT inhibitors, HDAC inhibitors, HSP90 inhibitors, mTOR inhibitors, PBK/niTGR inhibitors, PDK inhibitors, and antibody targeting tumor/cancer antigen to treat or ameliorate neoplastic disorders and/or inflammatory, autoimmune, or infectious disorders (WO 2011011199 A1).

The protein kinase CK2 has been shown to be involved in inflammation, pain, and certain immunological disorders, and other types of diseases such as diabetes, viral infection, neurodegenerative diseases (Borgo et al. Signal Transduction and Targeted Therapy, 183, 2021).

The development of a compound having a novel chemical structure different from that of known CK2 inhibitors and fully satisfiable as a drug for cancer treatment as well as a pharmaceutical composition containing the compound as an active ingredient has been desired. The requirements of antitumor therapeutics call for constant development of new anticancer agents with the aim of generating medicaments that are more potent and well tolerated. Thus, new antitumoral/anti-cancer compounds solving the aforementioned problems are desired.

SUMMARY

The present subject matter relates to the use of novel 3-substituted amino-2-arylpyrrolo[2,3-c]pyridine derivatives with improved potential for treating various types of cancer and with an increased probability of being active against drug resistance cancer cells. The requirements of antitumor therapeutics call for constant development of new anticancer agents with the aim of generating medicaments that are more potent and well tolerated.

The present subject matter relates the use of novel 3-substituted amino-2-arylpyrrolo[2,3-c]pyridine derivatives for treating kinase-associated conditions including inflammation, pain, and certain immunological disorders, and other types of diseases such as diabetes, viral infection, and neurodegenerative diseases.

The presently described compounds are not only new but have very valuable antitumoral properties. The compounds described herein demonstrated good to excellent cytotoxic property against a variety of cancer cell lines. The in vitro antitumoral property of the present molecules indicated high potency against PC3 prostate, HCT116 colon, A375 melanoma, H1299 lung, MIAPaCa-2 pancreas, HL60 leukemia, and MCF7 and MDA-MB-231 breast cancer cells with $IC_{50}$ values in the nano to micromolar concentration range after a 96 period of exposure. The 3-substituted amino-2-arylpyrrolo[2,3-c]pyridine compounds, showing inhibitory activity against CK2 enzyme, are potent anticancer agents and may find useful applications in cancer chemotherapy for the fight against various tumors.

The present subject matter provides novel 3-substituted amino-2-arylpyrrolo[2,3-c]pyridine compounds, for example, 3-substituted amino-2-arylpyrrolo[2,3-c]pyridine compounds of the general formula/structure I, as useful antitumor agents. The present subject matter further provides a process for the synthesis of such compounds, pharmaceutical compositions containing these compounds, and their use in therapy for the treatment of cancer as a sole active agent or in combination with other active ingredients.

In an embodiment, the present subject matter relates to a compound having the formula I:

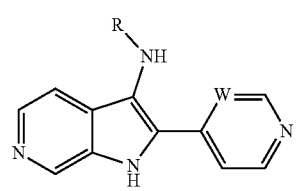

or a pharmaceutically acceptable salt, ester, stereoisomer, or solvate thereof, wherein:

W is CH or N;

R is selected from the group consisting of —Ar, —CH$_2$Ar, —COAr, —SO$_2$Ar, —CH$_2$CH$_2$NHR$_3$, —CH$_2$CH$_2$NR$_3$R$_4$, —CH$_2$CH$_2$CH$_2$NHR$_3$, —CH$_2$CH$_2$CH$_2$NR$_3$R$_4$, —COCH$_2$CH$_2$NHR$_3$, —COCH$_2$CH$_2$NR$_3$R$_4$, —COCH$_2$CH$_2$CH$_2$NHR$_3$, —COCH$_2$CH$_2$CH$_2$NR$_3$R$_4$, —SO$_2$CH$_2$CH$_2$NHR$_3$, —SO₂CH₂CH₂NR₃R₄, —SO₂CH₂CH₂CH₂NHR₃, and —SO₂CH₂CH₂CH₂NR₃R₄;

Ar is an aryl ring or a 5 or 6 membered heteroaryl ring, either of the aryl ring or the heteroaryl ring being optionally substituted with one or more substituents selected from the group consisting of halogen, cyano, —OH, —OR₁, —NH₂, —NHR₁, —NR₁R₂, —CONH₂, —CONHR₁, —CONR₁R₂, —SO₂NH₂, —SO₂NHR₁, —SO₂NR₁R₂, —NHCOR₁, —NHCO₂R₁, —NHCONHR₁, —NHSO₂NHR₁, —NHSO₂R₁, —COR₁, —CO₂R₁, C₁-C₆ straight chained alkyl, C₁-C₆ branched alkyl, C₃-C₆ cycloalkyl, halo-C₁-C₆ straight chain alkyl, halo-C₁-C₆ branched alkyl, halo-C₃-C₆ cycloalkyl, cyano-C₁-C₆ straight chain alkyl, cyano-C₁-C₆ branched alkyl, and cyano-C₃-C₆ cycloalkyl;

R₁ and R₂ are each independently selected from the group consisting of hydrogen, C₁-C₆ straight chain alkyl, C₁-C₆ branched alkyl, C₃-C₆ cycloalkyl, halo-C₁-C₆ straight chain alkyl, halo-C₁-C₆ branched alkyl, halo-C₃-C₆ cycloalkyl, cyano-C₁-C₆ straight chain alkyl, cyano-C₁-C₆ branched alkyl, and cyano-C₃-C₆ cycloalkyl; and R₃ and R₄ are each independently selected from the group consisting of hydrogen, C₁-C₆ straight chain alkyl, C₁-C₆ branched alkyl, C₃-C₆ cycloalkyl, halo-C₁-C₆ straight chain alkyl, halo-C₁-C₆ branched alkyl, halo-C₃-C₆ cycloalkyl, cyano-C₁-C₆ straight chain alkyl, cyano-C₁-C₆ branched alkyl, and cyano-C₃-C₆ cycloalkyl or wherein R₃ and R₄, together with a nitrogen atom to which they are attached, form a nitrogen-containing heterocycle, such nitrogen-containing heterocycle being optionally substituted with from one to three substituents independently selected from the group consisting of a straight or branched C₁-C₆ alkyl group, a halogen atom, a straight or branched C₁-C₆ alkoxy group, a straight or branched C₁-C₆ trihaloalkyl group, and a hydroxy group.

In another embodiment, the present subject matter relates to a compound having the formula I:

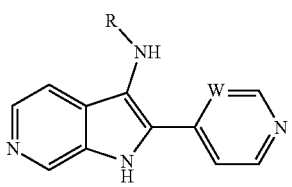

I or a pharmaceutically acceptable salt, ester, stereoisomer, or solvate thereof, wherein:

W is N or CH;

R is phenyl substituted with one or more substituents independently selected from the group consisting of —NR₁R₂, a straight or branched C₁-C₆ alkyl, —CONR₁R₂, and halogen, wherein R₁ and R₂ are independently a straight chain C₁-C₆ alkyl group; a —CH₂CH₂NR₃R₄ group; a —CH₂phenyl group substituted with a chlorine; a pyridin-2-yl group; a pyridin-3-ylmethyl group; and a —COphenyl group, wherein the phenyl group has one substituent selected from the group consisting of chlorine, methyl, and —N(CH₃)₂; and R₃ and R₄ are independently a straight chain C₁-C₆ alkyl group.

In a further embodiment, the present subject matter relates to a compound selected from the group consisting of: N-(3-chlorophenyl)-2-(pyridin-4-yl)-1H-pyrrolo[2,3-c]pyridin-3-amine (1), 2-(pyridin-4-yl)-N-(m-tolyl)-1H-pyrrolo[2,3-c]pyridin-3-amine (2), N,N-dimethyl-3-((2-(pyridin-4-yl)-1H-pyrrolo[2,3-c]pyridin-3-yl)amino)benzamide (3), N-(3-isopropylphenyl)-2-(pyridin-4-yl)-1H-pyrrolo[2,3-c]pyridin-3-amine (4), N1,N1-dimethyl-N3-(2-(pyridin-4-yl)-1H-pyrrolo[2,3-c]pyridin-3-yl)benzene-1,3-diamine (5), N-(pyridin-2-yl)-2-(pyridin-4-yl)-1H-pyrrolo[2,3-c]pyridin-3-amine (6), N-(3-chlorobenzyl)-2-(pyridin-4-yl)-1H-pyrrolo[2,3-c]pyridin-3-amine (7), N-(pyridin-3-ylmethyl)-2-(pyridin-4-yl)-1H-pyrrolo[2,3-c]pyridin-3-amine (8), N1,N1-dimethyl-N2-(2-(pyridin-4-yl)-1H-pyrrolo[2,3-c]pyridin-3-yl)ethane-1,2-diamine (9), 3-chloro-N-(2-(pyridin-4-yl)-1H-pyrrolo[2,3-c]pyridin-3-yl)benzamide (10), 3-methyl-N-(2-(pyridin-4-yl)-1H-pyrrolo[2,3-c]pyridin-3-yl)benzamide (11), 3-(dimethylamino)-N-(2-(pyridin-4-yl)-1H-pyrrolo[2,3-c]pyridin-3-yl)benzamide (12), N-(3-chlorophenyl)-2-(pyrimidin-4-yl)-1H-pyrrolo[2,3-c]pyridin-3-amine (13), N-(3-isopropylphenyl)-2-(pyrimidin-4-yl)-1H-pyrrolo[2,3-c]pyridin-3-amine (14), N-(3-chlorobenzyl)-2-(pyrimidin-4-yl)-1H-pyrrolo[2,3-c]pyridin-3-amine (15), and a pharmaceutically acceptable salt, ester, stereoisomer, or solvate thereof.

In an embodiment, the present subject matter relates to a process for the synthesis of the compounds of formula I, including a number of species or specific structures falling under structural formula I. Further contemplated herein are pharmaceutical compositions containing these compounds, as well as methods of inhibiting CK2 enzyme activity and of treating various cancers by administering the present compounds to a patient in need thereof.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., $C_1$-$C_{40}$ alkyl group), for example, 1-30 carbon atoms (i.e., $C_1$-$C_{30}$ alkyl group). In some embodiments, an alkyl group can have 1 to 6 carbon atoms, and can be referred to as a "lower alkyl group" or a "$C_1$-$C_6$ alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_2$-$C_{40}$ alkenyl group), for example, 2 to 20 carbon atoms (i.e., $C_2$-$C_{20}$ alkenyl group) or 2 to 6 carbon atoms (i.e., $C_2$-$C_6$ alkenyl group). In some embodiments, alkenyl groups can be substituted as described herein. An alkenyl group is generally not substituted with another alkenyl group, an alkyl group, or an alkynyl group.

The term "substituted alkyl" as used herein refers to an alkyl group in which 1 or more (up to about 5, for example about 3) hydrogen atoms is replaced by a substituent independently selected from the group: —O, —S, acyl, acyloxy, optionally substituted alkoxy, optionally substituted amino (wherein the amino group may be a cyclic amine), azido, carboxyl, (optionally substituted alkoxy)carbonyl, amido, cyano, optionally substituted cycloalkyl, optionally substituted cycloalkenyl, halogen, hydroxyl, nitro, sulfamoyl, sulfanyl, sulfinyl, sulfonyl, and sulfonic acid. Some of the optional substituents for alkyl are hydroxy, halogen exemplified by chloro and bromo, acyl exemplified by methylcarbonyl; alkoxy, and heterocyclyl exemplified by morpholino and piperidino. Other alkyl substituents as described herein may further be contemplated.

The term "substituted alkenyl" refers to an alkenyl group in which 1 or more (up to about 5, for example about 3) hydrogen atoms is replaced by a substituent independently selected from those listed above with respect to a substituted alkyl. Other alkenyl substituents as described herein may further be contemplated.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_6$-$C_{24}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —C6F5), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S-0 bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyrdazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats, and the like.

"Patient" as used herein refers to a subject in need of treatment of a condition, disorder, or disease, such as a CK2-associated condition, disorder, or disease, or cancer.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a compound having the formula I:

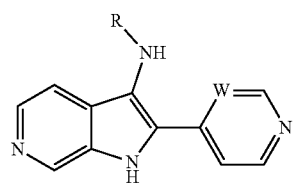

or a pharmaceutically acceptable salt, ester, stereoisomer, or solvate thereof, wherein:

W is CH or N;

R is selected from the group consisting of —Ar, —CH$_2$Ar, —COAr, —SO$_2$Ar, —CH$_2$CH$_2$NHR$_3$, —CH$_2$CH$_2$NR$_3$R$_4$, —CH$_2$CH$_2$CH$_2$NHR$_3$, —CH$_2$CH$_2$CH$_2$NR$_3$R$_4$, —COCH$_2$CH$_2$NHR$_3$, —COCH$_2$CH$_2$NR$_3$R$_4$, —COCH$_2$CH$_2$CH$_2$NHR$_3$, —COCH$_2$CH$_2$CH$_2$NR$_3$R$_4$, —SO$_2$CH$_2$CH$_2$NHR$_3$, —SO$_2$CH$_2$CH$_2$NR$_3$R$_4$, —SO$_2$CH$_2$CH$_2$CH$_2$NHR$_3$, and —SO$_2$CH$_2$CH$_2$CH$_2$NR$_3$R$_4$;

Ar is an aryl ring or a 5 or 6 membered heteroaryl ring, either of the aryl ring or the heteroaryl ring being optionally substituted with one or more substituents selected from the group consisting of halogen, cyano, —OH, —OR$_1$, —NH$_2$, —NHR$_1$, —NR$_1$R$_2$, —CONH$_2$, —CONHR$_1$, —CONR$_1$R$_2$, —SO$_2$NH$_2$, —SO$_2$NHR$_1$, —SO$_2$NR$_1$R$_2$, —NHCOR$_1$, —NHCO$_2$R$_1$, —NHCONHR$_1$, —NHSO$_2$NHR$_1$, —NHSO$_2$R$_1$, —COR$_1$, —CO$_2$R$_1$, C$_1$-C$_6$ straight chained alkyl, C$_1$-C$_6$ branched alkyl, C$_3$-C$_6$ cycloalkyl, halo-C$_1$-C$_6$ straight chain alkyl, halo-C$_1$-C$_6$ branched alkyl, halo-C$_3$-C$_6$ cycloalkyl, cyano-C$_1$-C$_6$ straight chain alkyl, cyano-C$_1$-C$_6$ branched alkyl, and cyano-C$_3$-C$_6$ cycloalkyl;

$R_1$ and $R_2$ are each independently selected from the group consisting of hydrogen, $C_1$-$C_6$ straight chain alkyl, $C_1$-$C_6$ branched alkyl, $C_3$-$C_6$ cycloalkyl, halo-$C_1$-$C_6$ straight chain alkyl, halo-$C_1$-$C_6$ branched alkyl, halo-$C_3$-$C_6$ cycloalkyl, cyano-$C_1$-$C_6$ straight chain alkyl, cyano-$C_1$-$C_6$ branched alkyl, and cyano-$C_3$-$C_6$ cycloalkyl; and $R_3$ and $R_4$ are each independently selected from the group consisting of hydrogen, $C_1$-$C_6$ straight chain alkyl, $C_1$-$C_6$ branched alkyl, $C_3$-$C_6$ cycloalkyl, halo-$C_1$-$C_6$ straight chain alkyl, halo-$C_1$-$C_6$ branched alkyl, halo-$C_3$-$C_6$ cycloalkyl, cyano-$C_1$-$C_6$ straight chain alkyl, cyano-$C_1$-$C_6$ branched alkyl, and cyano-$C_3$-$C_6$ cycloalkyl or wherein $R_3$ and $R_4$, together with a nitrogen atom to which they are attached, form a nitrogen-containing heterocycle, such nitrogen-containing heterocycle being optionally substituted with from one to three substituents independently selected from the group consisting of a straight or branched $C_1$-$C_6$ alkyl group, a halogen atom, a straight or branched $C_1$-$C_6$ alkoxy group, a straight or branched $C_1$-$C_6$ trihaloalkyl group, and a hydroxy group.

In a further embodiment, the present subject matter relates to compounds of formula I, wherein R is an optionally substituted —Ar group, an optionally substituted —CH$_2$Ar group, an optionally substituted —COAr group, or an optionally substituted —CH$_2$CH$_2$NR$_3$R$_4$ group.

In yet another embodiment, the present subject matter relates to compounds of formula I, wherein R is phenyl substituted with one or more substituents independently selected from the group consisting of —NR$_1$R$_2$, a straight or branched $C_1$-$C_6$ alkyl, —CONR$_1$R$_2$, and halogen. In a further embodiment, the present subject matter relates to compounds of formula I, wherein R is phenyl substituted with one or more substituents independently selected from the group consisting of methyl, —CON(CH$_3$)$_2$, isopropyl, chlorine, and —N(CH$_3$)$_2$.

In still yet another embodiment, the present subject matter relates to compounds of formula I, wherein R is a —CH$_2$CH$_2$NR$_3$R$_4$, wherein R$_3$ and R$_4$ are independently a straight chain $C_1$-$C_6$ alkyl group. In this regard, R$_3$ and R$_4$ can both be methyl.

In one embodiment, the present subject matter relates to a compound of formula I, wherein R is a —CH$_2$phenyl group substituted with a chlorine.

In another embodiment, the present subject matter relates to a compound of formula I, wherein R is a pyridin-2-yl group.

In a further embodiment, the present subject matter relates to a compound of formula I, wherein R is a pyridin-3-ylmethyl group.

In an additional embodiment, the present subject matter relates to a compound of formula I, wherein R is a —COphenyl group, wherein the phenyl group has one substituent selected from the group consisting of chlorine, methyl, and —N(CH$_3$)$_2$.

In an alternative embodiment, R$_3$ and R$_4$ can each independently be selected from the group consisting of hydrogen, a $C_1$-$C_6$ straight chain alkyl, a $C_1$-$C_6$ branched alkyl, a $C_3$-$C_6$ cycloalkyl, a halo-$C_1$-$C_6$ straight chain alkyl, a halo-$C_1$-$C_6$ branched alkyl, a halo-$C_3$-$C_6$ cycloalkyl, a cyano-$C_1$-$C_6$ straight chain alkyl, a cyano-$C_1$-$C_6$ branched alkyl, and a cyano-$C_3$-$C_6$ cycloalkyl.

In another embodiment, the present subject matter relates to a compound having the formula I:

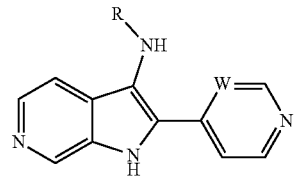

or a pharmaceutically acceptable salt, ester, stereoisomer, or solvate thereof, wherein:
W is N or CH;
R is phenyl substituted with one or more substituents independently selected from the group consisting of —NR$_1$R$_2$, a straight or branched $C_1$-$C_6$ alkyl, —CONR$_1$R$_2$, and halogen, wherein R$_1$ and R$_2$ are independently a straight chain $C_1$-$C_6$ alkyl group; a —CH$_2$CH$_2$NR$_3$R$_4$ group; a —CH$_2$phenyl group substituted with a chlorine; a pyridin-2-yl group; a pyridin-3-ylmethyl group; and a —COphenyl group, wherein the phenyl group has one substituent selected from the group consisting of chlorine, methyl, and —N(CH$_3$)$_2$; and
R$_3$ and R$_4$ are independently a straight chain $C_1$-$C_6$ alkyl group.

In a further embodiment, the present subject matter relates to a compound selected from the group consisting of: N-(3-chlorophenyl)-2-(pyridin-4-yl)-1H-pyrrolo[2,3-c]pyridin-3-amine (1), 2-(pyridin-4-yl)-N-(m-tolyl)-1H-pyrrolo[2,3-c]pyridin-3-amine (2), N,N-dimethyl-3-((2-(pyridin-4-yl)-1H-pyrrolo[2,3-c]pyridin-3-yl)amino)benzamide (3), N-(3-isopropylphenyl)-2-(pyridin-4-yl)-1H-pyrrolo[2,3-c]pyridin-3-amine (4), N1,N1-dimethyl-N3-(2-(pyridin-4-yl)-1H-pyrrolo[2,3-c]pyridin-3-yl)benzene-1,3-diamine (5), N-(pyridin-2-yl)-2-(pyridin-4-yl)-1H-pyrrolo[2,3-c]pyridin-3-amine (6), N-(3-chlorobenzyl)-2-(pyridin-4-yl)-1H-pyrrolo[2,3-c]pyridin-3-amine (7), N-(pyridin-3-ylmethyl)-2-(pyridin-4-yl)-1H-pyrrolo[2,3-c]pyridin-3-amine (8), N1,N1-dimethyl-N2-(2-(pyridin-4-yl)-1H-pyrrolo[2,3-c]pyridin-3-yl)ethane-1,2-diamine (9), 3-chloro-N-(2-(pyridin-4-yl)-1H-pyrrolo[2,3-c]pyridin-3-yl)benzamide (10), 3-methyl-N-(2-(pyridin-4-yl)-1H-pyrrolo[2,3-c]pyridin-3-yl)benzamide (11), 3-(dimethylamino)-N-(2-(pyridin-4-yl)-1H-pyrrolo[2,3-c]pyridin-3-yl)benzamide (12), N-(3-chlorophenyl)-2-(pyrimidin-4-yl)-1H-pyrrolo[2,3-c]pyridin-3-amine (13), N-(3-isopropylphenyl)-2-(pyrimidin-4-yl)-1H-pyrrolo[2,3-c]pyridin-3-amine (14), N-(3-chlorobenzyl)-2-(pyrimidin-4-yl)-1H-pyrrolo[2,3-c]pyridin-3-amine (15), and a pharmaceutically acceptable salt, ester, stereoisomer, or solvate thereof.

Said differently, the present subject matter can relate to compounds of formula I selected from the group consisting of:

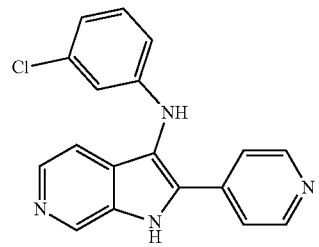

| | |
|---|---|
| 2 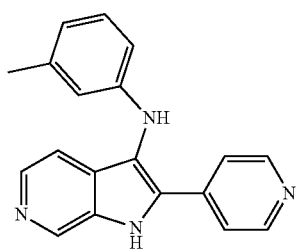 | 8 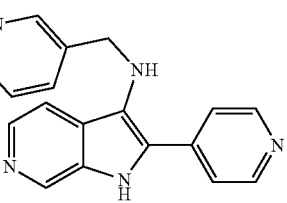 |
| 3 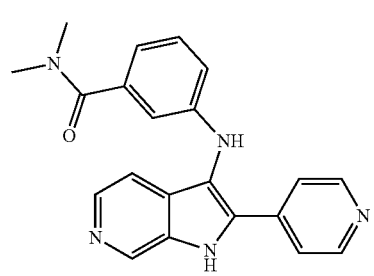 | 9 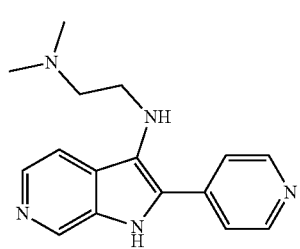 |
| 4 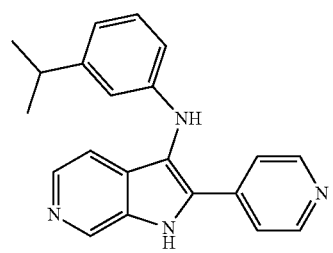 | 10 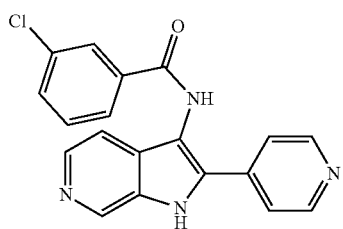 |
| 5 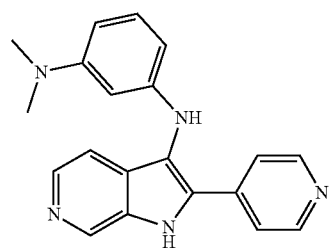 | 11 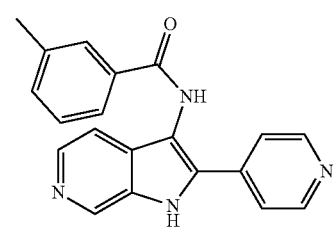 |
| 6 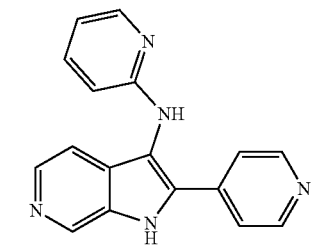 | 12 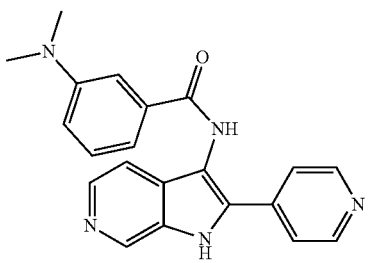 |
| 7 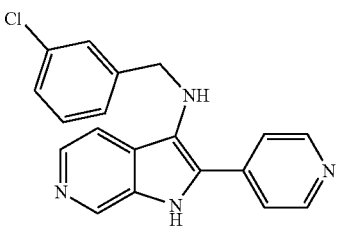 | 13 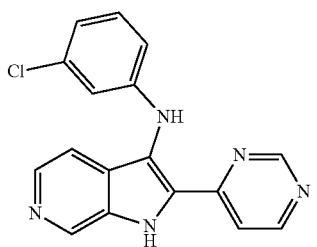 |

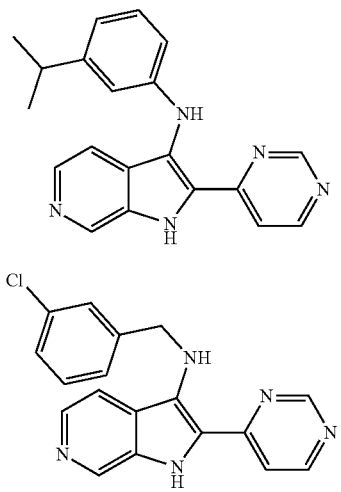

and a pharmaceutically acceptable salt, ester, stereoisomer, or solvate thereof.

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formula I and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers, and the salts of the stereoisomers thereof may contain, e.g., when isolated in crystalline form, varying amounts of solvents. Included within the present scope are, therefore, all solvates of the compounds of formula I, as well as the solvates of the salts, the stereoisomers, and the salts of the stereoisomers of the compounds of formula I.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula I and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

In one embodiment, the present compounds can be prepared according to the following general synthetic pathway. Specifically, synthesis commences with adding, to a mixture of 4-bromopyridin-3-amine I, $Pd_2dba_3$, XPhos, and t-BuONa in butanol, bromovinyl derivative II. The reaction mixture is heated to a temperature of about 112° C. for at least about 24 hours under a nitrogen atmosphere. The solvent is concentrated under reduced pressure. The resulting residue is diluted with $CH_2Cl_2$ and $NH_4Cl$ saturated solution. The combined organic layers are dried with anhydrous magnesium sulfate, filtered, and concentration. The resulting crude product is purified to provide the corresponding 2-heteroarylpyrrolo[2,3-c]pyridine III as outlined in Scheme 1.

Scheme 1

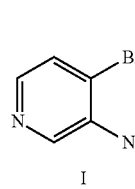 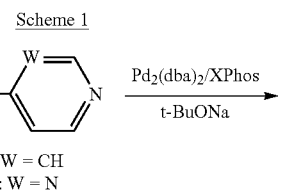

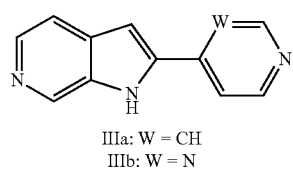

Next, to a solution of 2-heteroarylpyrrolo[2,3-c]pyridine III in DMF is added dropwise at room temperature a solution of N-bromosuccinimide in DMF and the mixture is stirred for at least about 16 hours. The solvent is concentrated under reduced pressure and the crude product is dissolved in $CH_2Cl_2$ and washed with a brine saturated solution. The organic layer is dried over $MgSO_4$, filtrated, and concentrated under reduced pressure. The resulting crude residue is then purified to afford the corresponding bromide derivatives IV as outlined in Scheme 2.

Scheme 2

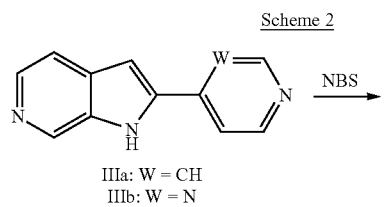

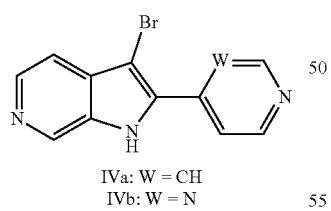

To synthesize the derivatives 1-6, 13, and 14, a mixture of the bromide derivative IV and arylamine, $Pd(OAc)_2$, BINAP, and t-BuONa in toluene is heated as about 65° C. to about 75° C. under a nitrogen atmosphere for at least about 8 hours. The reaction mixture is diluted with ethyl acetate and water. The organic layer is separated, washed with brine, dried over anhydrous $MgSO_4$, and concentrated under reduced pressure to obtain the crude product, which is purified to provide the derivatives 1-6, 13, and 14 as outlined in Scheme 3.

Scheme 3

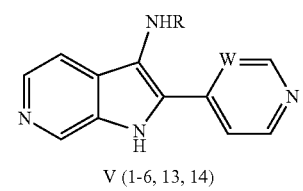

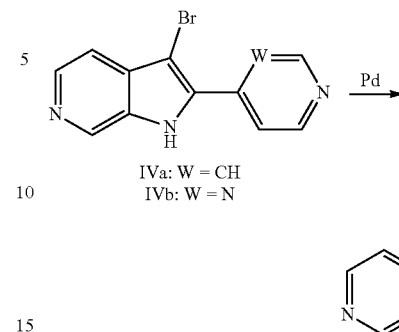

V (1-6, 13, 14)

Alternatively, a mixture of 2-heteroarylpyrrolo[2,3-c]pyridine III, $K_2S_2O_8$ and $NaNO_2$ in DMF is heated at about 75° C. to about 85° C. for at least about 4 hours. The reaction mixture is allowed to cool, diluted with water, and then extracted with ethyl acetate. The combined organic layers are dried over anhydrous $MgSO_4$, filtrated and concentrated under vacuum. The resulting crude product is then purified to provide the corresponding 2-heteroaryl-3-nitropyrrolo[2,3-c]pyridine which is engaged in the next step.

A mixture of 2-heteroaryl-3-nitropyrrolo[2,3-c]pyridine and 10% Pd/C in methanol is stirred at room temperature under a hydrogen atmosphere for at least about 5 hours. After removing the catalyst by filtration, the filtrate is concentrated to give the crude product, which is purified to yield the 3-amino-2-heteroarylpyrrolo[2,3-c]pyridine VI as shown in Scheme 4.

Scheme 4

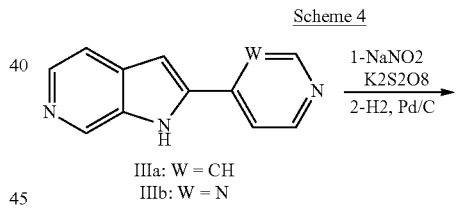

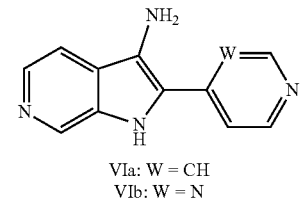

To synthesize the derivatives 7, 8, and 15, a mixture of 3-amino-2-heteroarylpyrrolo[2,3-c]pyridine VI and an aldehyde derivative is stirred at room temperature. After stirring for at least about 2 hours, sodium cyanoborohydride is added by small portions to the reaction mixture and stirred at room temperature for an additional at least about 2 hours. The solvent is then concentrated under vacuum and the resulting crude product is diluted in $CH_2Cl_2$ and washed with 10% HCl. The organic layer is dried over anhydrous magnesium sulfate, filtrated, and concentrated to afford the residue, which is purified to give the corresponding 3-N-benzylamino-2-heteroarylpyrrolo[2,3-c]pyridine 7, 8, and 15 as outlined in Scheme 5.

Scheme 5

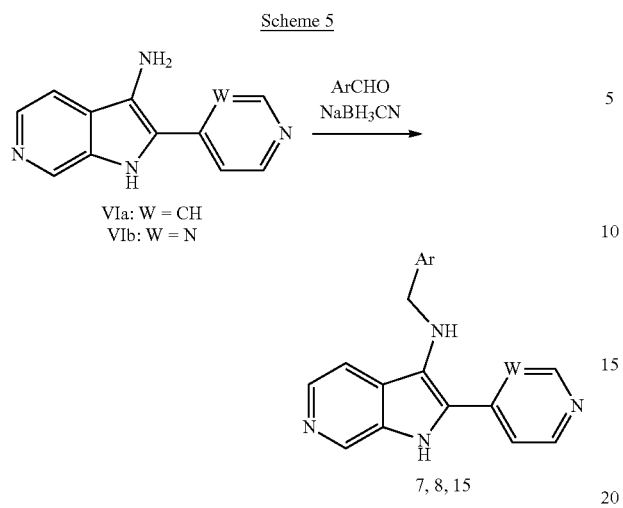

7, 8, 15

To synthesize the derivatives 10-12, to a solution of 2-(pyridin-4-yl)-1H-pyrrolo[2,3-c]pyridin-3-amine VIa and triethyl amine in $CH_2Cl_2$ is added a solution of benzoyl chloride in $CH_2Cl_2$ and the reaction mixture is stirred at room temperature for at least about 1 hour. The reaction mixture is washed with 10% NaOH. The organic layer is dried over anhydrous magnesium sulfate, filtrated, and concentrated to afford the residue, which is purified to provide the corresponding 3-N-benzoylamino-2-heteroarylpyrrolo[2,3-c]pyridine 10-12 as outlined in Scheme 6.

Scheme 6

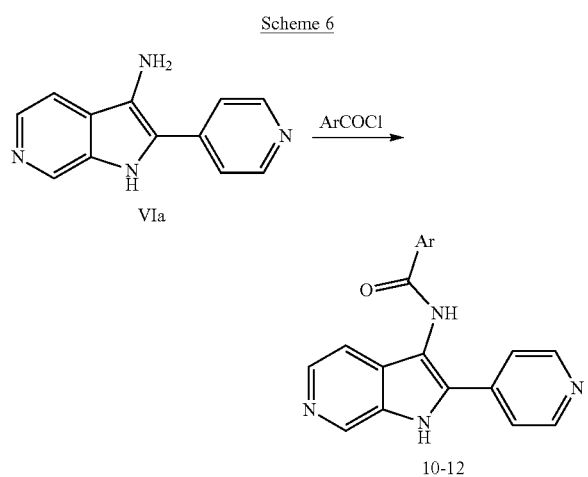

10-12

To synthesize the derivative 9, to a solution of 2-(pyridin-4-yl)-1H-pyrrolo[2,3-c]pyridin-3-amine VIa in DMF is added triethyl amine, potassium iodide, and 2-chloro-N,N-dimethylethan-1-amine and the reaction mixture is stirred at room temperature for at least about 18 hours. The reaction solvent is concentrated under vacuum and the resulting crude product is treated with 10% NaOH and extracted with $CH_2Cl_2$. The combined organic layers are dried over anhydrous magnesium sulfate, filtrated, and concentrated to afford the residue, which is purified by silica gel column chromatography to yield N1,N1-dimethyl-N2-(2-(pyridin-4-yl)-1H-pyrrolo[2,3-c]pyridin-3-yl)ethane-1,2-diamine 9 as outlined in Scheme 7.

Scheme 7

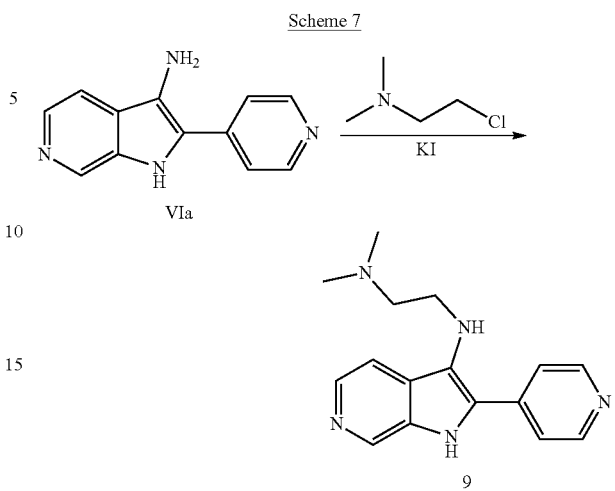

9

In another embodiment, the present subject matter is directed to pharmaceutical compositions comprising a therapeutically effective amount of the compounds as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

In an embodiment, the pharmaceutical composition comprises one or two of the present compounds, or one of the present compounds.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for cancer. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of cancer, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present compounds have valuable pharmaceutical properties, which make them commercially utilizable. Accordingly, the present subject matter further relates to use of the present compounds for the treatment of diseases such as cancers. Similarly, the present compounds can be used to inhibit CK2 enzyme activity in a patient.

In another embodiment of the present subject matter, the aforementioned compound derivatives demonstrated in vitro anticancer action against human cancer cell lines such as MCF7 and MDA-MB-231 (breast cancer), H1299 (lung cancer), PC3 (prostate cancer), HCT116 (colon cancer), A375 (melanoma), MIAPaCa2 (pancreatic cancer), and HL60 (leukemia). Accordingly, the present subject matter relates to methods of treating a cancer in a patient by administering one or more of the compounds presented herein to a patient in need thereof. In certain embodiments, the cancer treatable with the present compounds is one or more selected from the group consisting of leukemia, melanoma, colon cancer, prostate cancer, lung cancer, pancreatic cancer, and breast cancer.

Accordingly, in an embodiment of the present subject matter, the 3-substituted amino-2-arylpyrrolo[2,3-c]pyridine derivatives as described herein engaged for in vitro study towards human cancer cell lines can display an $IC_{50}$ with a nano to micromolar concentration range when exposed to a period of at least 96 hrs. For example, a present compound engaged for in vitro study against PC3 (prostate) cancer cell lines can display an $IC_{50}$ concentration of 1.5 µM at an exposure period of at least 96 hrs.

In another embodiment, a present compound engaged for in vitro study against HCT116 (colon) cancer cell lines can display an $IC_{50}$ concentration of 1.9 µM at an exposure period of at least 96 hrs.

In a further embodiment, a present compound engaged for in vitro study against A375 (melanoma) cancer cell lines can display an $IC_{50}$ concentration of 3.2 µM at an exposure period of at least 96 hrs.

In an embodiment, a present compound engaged for in vitro study against H1299 (lung) cancer cell lines can display an $IC_{50}$ concentration of 1.4 µM at an exposure period of at least 96 hrs.

In another embodiment, a present compound engaged for in vitro study against MIAPaCa-2 (pancreas) cancer cell lines can display an $IC_{50}$ concentration of 1.9 µM at an exposure period of at least 96 hrs.

In a further embodiment, a present compound engaged for in vitro study against HL60 (leukemia) cancer cell lines can display an $IC_{50}$ concentration of 4.1 µM at an exposure period of at least 96 hrs.

In one embodiment, a present compound engaged for in vitro study against MCF7 (breast) cancer cell lines can display an $IC_{50}$ concentration of 5.2 µM at an exposure period of at least 96 hrs.

In another embodiment, a present compound engaged for in vitro study against MDA-MB-231 (breast) cancer cell lines can display an $IC_{50}$ concentration of 4.3 µM at an exposure period of at least 96 hrs.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one or two of the present compounds are used, or one of the present compounds is used. Similarly, one or more of the present compounds can be used in combination therapy with one or more additional active agents.

The following examples relate to various methods of manufacturing certain specific compounds as described herein. All compound numbers expressed herein are with reference to the synthetic pathway figures shown above.

EXAMPLES

Example 1

General Preparation of 2-heteroarylpyrrolo[2,3-c]pyridine III

To a mixture of 4-bromopyridin-3-amine 1 (2 mmol), $Pd_2dba_3$ (0.08 mmol), XPhos (0.16 mmol), and t-BuONa (6 mmol) in butanol (15 mL) was added bromovinyl derivative II (3 mmol) and the reaction was heated at 110° C. for 24 h under nitrogen atmosphere. The solvent was concentrated under reduced pressure and the resulting residue was diluted with $CH_2Cl_2$ (10 mL) and $NH_4Cl$ saturated solution (10 mL). The aqueous layer was then extracted with $CH_2Cl_2$ (4×5 mL). The combined organic layers were dried with anhydrous magnesium sulfate, filtered, and concentrated. The resulting crude product was purified by silica gel column chromatography to afford the corresponding 2-heteroarylpyrrolo[2,3-c]pyridine III.

Example 2

Preparation of 2-(pyridin-4-yl)-1H-pyrrolo[2,3-c]pyridine IIIa

The expected product was obtained in accordance with the general procedure for the preparation of 2-heteroarylpyrrolo[2,3-c]pyridine III of Example 1 using 4-(1-bromovinyl)pyridine IIa as bromovinyl derivative II.

Elemental Analysis: Calculated C, 73.83; H, 4.65; N, 21.52; Found C, 73.80; H, 4.68; N, 21.55.

Example 3

Preparation of 2-(pyrimidin-4-yl)-1H-pyrrolo[2,3-c]pyridine IIIb

The expected product was obtained in accordance with the general procedure for the preparation of 2-heteroarylpyrrolo[2,3-c]pyridine III of Example 1 using 4-(1-bromovinyl)pyrimidine IIb as bromovinyl derivative II.

Elemental Analysis: Calculated C, 67.34; H, 4.11; N, 28.55; Found C, 67.31; H, 4.09; N, 28.53.

Example 4

General method for the bromination reaction of 2-heteroarylpyrrolo[2,3-c]pyridine III To a solution of 2-heteroarylpyrrolo[2,3-c]pyridine III (4 mmol) in DMF (15 mL) was added dropwise at room temperature a solution of N-bromosuccinimide(4 mmol) in DMF (15 mL) and the mixture was stirred for 16 hours. The solvent was concentrated under reduced pressure and the crude product was dissolved in $CH_2Cl_2$ (15 mL) and washed with a brine saturated solution. The organic layer was dried over anhydrous magnesium sulfate, filtrated and concentrated under reduced pressure. The resulting crude residue was purified by silica-gel column chromatography to afford the corresponding bromide derivatives IV.

Example 5

Preparation of 3-bromo-2-(pyridin-4-yl)-1H-pyrrolo [2,3-c]pyridine IVa

The expected product was obtained in accordance with the general procedure for the bromination reaction of 2-heteroarylpyrrolo[2,3-c]pyridine III of Example 4 using 2-(pyridin-4-yl)-1H-pyrrolo[2,3-c]pyridine IIIa as 2-heteroarylpyrrolo[2,3-c]pyridine III.

Elemental Analysis: Calculated C, 52.58; H, 2.94; N, 15.33; Found C, 52.55; H, 2.96; N, 15.37.

Example 6

Preparation of 3-bromo-2-(pyrimidin-4-yl)-1H-pyrrolo[2,3-c]pyridine IVb

The expected product was obtained in accordance with the general procedure for the bromination reaction of 2-heteroarylpyrrolo[2,3-c]pyridine III of Example 4 using 2-(pyrimidin-4-yl)-1H-pyrrolo[2,3-c]pyridine IIIb as 2-heteroarylpyrrolo[2,3-c]pyridine III.

Elemental Analysis: Calculated C, 48.02; H, 2.56; N, 20.37; Found C, 47.99; H, 2.59; N, 20.34.

Example 7

General preparation of 3-substituted amino-2-heteroarylpyrrolo[2,3-c]pyridine V

A mixture of the bromide derivative IV (1.0 mmol) and arylamine (1.2 mmol), $Pd(OAc)_2$ (0.1 mmol), BINAP (0.15 mmol), and t-BuONa (2 mmol) in toluene (5 mL) was heated at 70° C. under nitrogen atmosphere for 8 hours. The reaction mixture was diluted with ethyl acetate (10 mL) and water (10 mL). The organic layer was separated, washed with brine, dried over anhydrous magnesium sulfate and concentrated under reduced pressure to obtain the crude product which was purified by silica gel column chromatography to provide the derivatives 1-6, 13 and 14.

Example 8

Preparation of N-(3-chlorophenyl)-2-(pyridin-4-yl)-1H-pyrrolo[2,3-c]pyridin-3-amine (1)

The expected product was obtained in accordance with the general procedure for the preparation of 3-substituted amino-2-heteroarylpyrrolo[2,3-c]pyridine V of Example 7 using 3-bromo-2-(pyridin-4-yl)-1H-pyrrolo[2,3-c]pyridine IVa as bromide derivative IV and 3-chloroaniline as the arylamine.

Elemental Analysis: Calculated C, 67.40; H, 4.09; N, 17.47; Found C, 67.35; H, 4.11; N, 17.44.

Example 9

Preparation of 2-(pyridin-4-yl)-N-(m-tolyl)-1H-pyrrolo[2,3-c]pyridin-3-amine (2)

The expected product was obtained in accordance with the general procedure for the preparation of 3-substituted amino-2-heteroarylpyrrolo[2,3-c]pyridine V of Example 7 using 3-bromo-2-(pyridin-4-yl)-1H-pyrrolo[2,3-c]pyridine IVa as bromide derivative IV and m-toluidine as the arylamine.

Elemental Analysis: Calculated C, 75.98; H, 5.37; N, 18.65; Found C, 76.01; H, 5.33; N, 18.68.

Example 10

Preparation of N,N-dimethyl-3-((2-(pyridin-4-yl)-1H-pyrrolo[2,3-c]pyridin-3-yl)amino)benzamide (3)

The expected product was obtained in accordance with the general procedure for the preparation of 3-substituted amino-2-heteroarylpyrrolo[2,3-c]pyridine V of Example 7 using 3-bromo-2-(pyridin-4-yl)-1H-pyrrolo[2,3-c]pyridine IVa as bromide derivative IV and 3-amino-N,N-dimethylbenzamide as the arylamine.

Elemental Analysis: Calculated C, 70.57; H, 5.36; N, 19.59; Found C, 70.53; H, 5.34; N, 19.61.

Example 11

Preparation of N-(3-isopropylphenyl)-2-(pyridin-4-yl)-1H-pyrrolo[2,3-c]pyridin-3-amine (4)

The expected product was obtained in accordance with the general procedure for the preparation of 3-substituted amino-2-heteroarylpyrrolo[2,3-c]pyridine V of Example 7 using 3-bromo-2-(pyridin-4-yl)-1H-pyrrolo[2,3-c]pyridine IVa as bromide derivative IV and 3-isopropylaniline as the arylamine.

Elemental Analysis: Calculated C, 76.80; H, 6.14; N, 17.06; Found C, 76.77; H, 6.18; N, 17.02.

Example 12

Preparation of N1,N1-dimethyl-N3-(2-(pyridin-4-yl)-1H-pyrrolo[2,3-c]pyridin-3-yl)benzene-1,3-diamine (5)

The expected product was obtained in accordance with the general procedure for the preparation of 3-substituted amino-2-heteroarylpyrrolo[2,3-c]pyridine V of Example 7 using 3-bromo-2-(pyridin-4-yl)-1H-pyrrolo[2,3-c]pyridine IVa as bromide derivative IV and 3-dimethylaminoaniline as the arylamine.

Elemental Analysis: Calculated C, 72.92; H, 5.81; N, 21.26; Found C, 72.89; H, 5.77; N, 21.29.

Example 13

Preparation of N-(pyridin-2-yl)-2-(pyridin-4-yl)-1H-pyrrolo[2,3-c]pyridin-3-amine (6)

The expected product was obtained in accordance with the general procedure for the preparation of 3-substituted amino-2-heteroarylpyrrolo[2,3-c]pyridine V of Example 7 using 3-bromo-2-(pyridin-4-yl)-1H-pyrrolo[2,3-c]pyridine IVa as bromide derivative IV and 2-aminopyridine as the arylamine.

Elemental Analysis: Calculated C, 71.06; H, 4.56; N, 24.37; Found C, 71.03; H, 4.59; N, 24.36.

Example 14

Preparation of N-(3-chlorophenyl)-2-(pyrimidin-4-yl)-1H-pyrrolo[2,3-c]pyridin-3-amine (13)

The expected product was obtained in accordance with the general procedure for the preparation of 3-substituted amino-2-heteroarylpyrrolo[2,3-c]pyridine V of Example 7 using 3-bromo-2-(pyrimidin-4-yl)-1H-pyrrolo[2,3-c]pyridine IVb as bromide derivative IV and 3-chloroaniline as the arylamine.

Elemental Analysis: Calculated C, 63.46; H, 3.76; N, 21.77; Found C, 63.48; H, 3.72; N, 21.80.

Example 15

Preparation of N-(3-isopropylphenyl)-2-(pyrimidin-4-yl)-1H-pyrrolo[2,3-c]pyridin-3-amine The expected product was obtained in accordance with the general procedure for the preparation of 3-substituted amino-2-heteroarylpyrrolo[2,3-c]pyridine V of Example 7 using 3-bromo-2-(pyrimidin-4-yl)-1H-pyrrolo[2,3-c]pyridine IVb as bromide derivative IV and 3-isopropylaniline as the arylamine.

Elemental Analysis: Calculated C, 72.92; H, 5.81; N, 21.26; Found C, 72.88; H, 5.76; N, 21.29.

Example 16

General preparation of 3-amino-2-heteroarylpyrrolo[2,3-c]pyridine VI

A mixture of 2-heteroarylpyrrolo[2,3-c]pyridine III (2 mmol), $K_2S_2O_8$ (4 mmol), and $NaNO_2$ (8 mmol) in DMF (5 mL) was heated at 80° C. for 4 hours. The reaction mixture was allowed to cool, diluted with water (10 mL) and then extracted with ethyl acetate (3×10 mL). The combined organic layers were dried over anhydrous $MgSO_4$, filtrated, and concentrated under vacuum to provide the crude product, which was purified by silica gel column chromatography to afford the corresponding 2-heteroaryl-3-nitropyrrolo[2,3-c]pyridine, which was engaged in the next step.

A mixture of 2-heteroaryl-3-nitropyrrolo[2,3-c]pyridine (3 mmol) and 10% Pd/C (35 mg) in methanol (10 mL) was stirred at room temperature under hydrogen atmosphere for 5 hours. After removing the catalyst by filtration, the filtrate was concentrated to give the crude product, which was purified by silica gel column chromatography to yield the 3-amino-2-heteroarylpyrrolo[2,3-c]pyridine VI.

Example 17

Preparation of 2-(pyridin-4-yl)-1H-pyrrolo[2,3-c]pyridine-3-amine VIa

The expected product was obtained in accordance with the general procedure for the method of preparation of 3-amino-2-heteroarylpyrrolo[2,3-c]pyridine VI of Example 16 using 2-(pyridin-4-yl)-1H-pyrrolo[2,3-c]pyridine IIIa as 2-heteroarylpyrrolo[2,3-c]pyridine III.

Elemental Analysis: Calculated C, 68.56; H, 4.79; N, 26.65; Found C, 68.54; H, 4.75; N, 26.69.

Example 18

Preparation of 2-(pyrimidin-4-yl)-1H-pyrrolo[2,3-c]pyridine-3-amine VIb

The expected product was obtained in accordance with the general procedure for the method of preparation of 3-amino-2-heteroarylpyrrolo[2,3-c]pyridine VI of Example 16 using 2-(pyrimidin-4-yl)-1H-pyrrolo[2,3-c]pyridine IIIb as 2-heteroarylpyrrolo[2,3-c]pyridine III.

Elemental Analysis: Calculated C, 62.55; H, 4.29; N, 33.16; Found C, 62.58; H, 4.31; N, 33.12.

Example 19

General preparation of 3-N-benzylamino-2-heteroarylpyrrolo[2,3-c]pyridine (7), (8), and (15)

A mixture of 3-amino-2-heteroarylpyrrolo[2,3-c]pyridine VI (1 mmol) and an aldehyde derivative (1.2 mmol) was stirred at room temperature. After stirring for 2 hours, sodium cyanoborohydride (2 mmol) was added by a small portion to the reaction mixture and stirred at room temperature for an additional 2 hours. The solvent was then concentrated under vacuum and the resulting crude product was diluted in $CH_2Cl_2$ (15 mL) and washed with 10% HCl (3×10 mL). The organic layer was dried over anhydrous magnesium sulfate, filtrated and concentrated to afford the residue which was purified by silica gel column chromatography to give the corresponding 3-N-benzylamino-2-heteroarylpyrrolo[2,3-c]pyridines 7, 8 and 15.

Example 20

Preparation of N-(3-chlorobenzyl)-2-(pyridin-4-yl)-1H-pyrrolo[2,3-c]pyridin-3-amine (7)

The expected product was obtained in accordance with the general procedure for the preparation of 3-N-benzylamino-2-heteroarylpyrrolo[2,3-c]pyridine 7, 8 and 15 of Example 19 using 2-(pyridin-4-yl)-1H-pyrrolo[2,3-c]pyridin-3-amine VIa as 3-amino-2-heteroarylpyrrolo[2,3-c]pyridine VI and 3-chlorobenzaldehyde as the aldehyde derivative.

Elemental Analysis: Calculated C, 68.16; H, 4.52; N, 16.73; Found C, 68.13; H, 4.48; N, 16.75.

Example 21

Preparation of N-(pyridin-3-ylmethyl)-2-(pyridin-4-yl)-1H-pyrrolo[2,3-c]pyridin-3-amine (8)

The expected product was obtained in accordance with the general procedure for the preparation of 3-N-benzylamino-2-heteroarylpyrrolo[2,3-c]pyridine 7, 8 and 15 of Example 19 using 2-(pyridin-4-yl)-1H-pyrrolo[2,3-c]pyridin-3-amine VIa as 3-amino-2-heteroarylpyrrolo[2,3-c]pyridine VI and nicotinaldehyde as the aldehyde derivative.

Elemental Analysis: Calculated C, 71.74; H, 5.02; N, 23.24; Found C, 71.70; H, 4.98; N, 23.27.

Example 22

Preparation of N-(3-chlorobenzyl)-2-(pyrimidin-4-yl)-1H-pyrrolo[2,3-c]pyridin-3-amine (15)

The expected product was obtained in accordance with the general procedure for the preparation of 3-N-benzylamino-2-heteroarylpyrrolo[2,3-c]pyridine 7, 8 and 15 of Example 19 using 2-(pyrimidin-4-yl)-1H-pyrrolo[2,3-c]pyridin-3-amine VIb as 3-amino-2-heteroarylpyrrolo[2,3-c]pyridine VI and 3-chlorobenzaldehyde as the aldehyde derivative.

Elemental Analysis: Calculated C, 64.38; H, 4.20; N, 20.86; Found C, 64.34; H, 4.17; N, 20.83.

Example 23

General preparation of 3-N-benzoylamino-2-heteroarylpyrrolo[2,3-c]pyridine (10)-(12)

To a solution of 2-(pyridin-4-yl)-1H-pyrrolo[2,3-c]pyridin-3-amine VIa (1 mmol) and triethyl amine (1.5 mmol) in $CH_2Cl_2$ (10 mL) was added a solution of benzoyl chloride (1.2 mmol) in $CH_2Cl_2$ (5 mL) and the reaction mixture was stirred at room temperature for 1 hour. The reaction mixture was washed with 10% NaOH (4×5 mL). The organic layer was dried over anhydrous magnesium sulfate, filtrated and concentrated to afford the residue which was purified by silica gel column chromatography to provide the corresponding 3-N-benzoylamino-2-heteroarylpyrrolo[2,3-c]pyridines 10-12.

Example 24

Preparation of 3-chloro-N-(2-(pyridin-4-yl)-1H-pyrrolo[2,3-c]pyridin-3-yl)benzamide (10)

The expected product was obtained in accordance with the general procedure for the preparation of 3-N-benzoylamino-2-heteroarylpyrrolo[2,3-c]pyridine 10-12 of Example 23 using 3-chlorobenzoyl chloride as the benzoyl chloride.

Elemental Analysis: Calculated C, 65.43; H, 3.76; N, 16.06; Found C, 65.41 H, 3.73; N, 16.02.

Example 25

Preparation of 3-methyl-N-(2-(pyridin-4-yl)-1H-pyrrolo[2,3-c]pyridin-3-yl)benzamide (11)

The expected product was obtained in accordance with the general procedure for the preparation of 3-N-benzoylamino-2-heteroarylpyrrolo[2,3-c]pyridine 10-12 of Example 23 using 3-methylbenzoyl chloride as the benzoyl chloride.

Elemental Analysis: Calculated C, 73.15; H, 4.91; N, 17.06; Found C, 73.11; H, 4.87; N, 17.04.

Example 26

Preparation of 3-(dimethylamino)-N-(2-(pyridin-4-yl)-1H-pyrrolo[2,3-c]pyridin-3-yl)benzamide (12)

The expected product was obtained in accordance with the general procedure for the preparation of 3-N-benzoylamino-2-heteroarylpyrrolo[2,3-c]pyridine 10-12 of Example 23 using 3-(dimethylamino)benzoyl chloride as the benzoyl chloride.

Elemental Analysis: Calculated C, 70.57; H, 5.36; N, 19.59; Found C, 70.61; H, 5.33; N, 19.62.

Example 27

Preparation of N1,N1-dimethyl-N2-(2-(pyridin-4-yl)-1H-pyrrolo[2,3-c]pyridin-3-yl)ethane-1,2-diamine (9)

To a solution of 2-(pyridin-4-yl)-1H-pyrrolo[2,3-c]pyridin-3-amine VIa (1 mmol) in DMF (10 mL) were added triethyl amine (1.5 mmol), potassium iodide (1.2 mmol), and 2-chloro-N,N-dimethylethan-1-amine (1.2 mmol), and the reaction mixture was stirred at room temperature for 18 hours. The reaction solvent was concentrated under vacuum and the resulting crude product was treated with 10% NaOH (10 mL) and extracted with $CH_2Cl_2$ (3×5 mL). The combined organic layers were dried over anhydrous magnesium sulfate, filtrated, and concentrated to afford the residue which was purified by silica gel column chromatography to yield N1,N1-dimethyl-N2-(2-(pyridin-4-yl)-1H-pyrrolo[2,3-c]pyridin-3-yl)ethane-1,2-diamine 9.

Elemental Analysis: Calculated C, 68.30; H, 6.81; N, 24.89; Found C, 68.27; H, 6.83; N, 24.92.

Pharmacological Activity

Example 28

In vitro Cytotoxic Activity Assay

Compounds 1-15 were screened for their in vitro cytotoxic activity utilizing a 3-(4,5-dimethyl-thiazol-2-yl)-2,5-diphenyltetrazolium bromide (MTT) assay against selected cancer human cell lines consisting of PC3 (prostate), HCT116 (colon), A375 (melanoma), H1299 (lung), MIAPaCa-2 (pancreas), HL60 (leukemia), MCF7 (breast), MDA-MB-231 (breast) (T. Mosmann, J. Immunol. Meth., 1983, 65, 55-63). The cells were cultured at 37° C. in RMPI1640 medium supplemented with 10% fetal bovine serum, 50 IU/mL penicillin, and 50 µg/mL streptomycin in a 5% $CO_2$ incubator. All cells were sub-cultured 3 times/week by trypsinisation. Viable cells were seeded and allowed to adhere for 12 h before a test drug was added in 96-well plates at an initial density of $1.0×10^5$ cells/mL. Tumour cell lines were separately exposed to various concentrations of the tested compounds followed by incubation at a temperature of 37° C. during 96 h inside a medium of fresh RMPI 1640. Cells were subsequently incubated at 37° C. using MTT at 0.5 mg/mL during 4 h. After removal of supernatant, formazan crystals were dissolved in isopropanol and the optical density was measured at 570 nm. CX-4945 was used as a positive control.

By way of example, the compound (13) displayed promising anti-proliferative activity against human cancer cells as reported in Table 1.

TABLE 1

Cytotoxicity activity of compound of Example 13 and CX-4945 on various human cancer cells[a]

| Cancer cell lines | Example 13 | CX-4945 |
| --- | --- | --- |
| PC3 (prostate) | 1.5 | 2.0 |
| HCT116 (colon) | 1.9 | 2.3 |

TABLE 1-continued

Cytotoxicity activity of compound of Example 13
and CX-4945 on various human cancer cells[a]

| Cancer cell lines | Example 13 | CX-4945 |
|---|---|---|
| A375 (melanoma) | 3.2 | 4.1 |
| H1299 (lung) | 1.4 | 2.3 |
| MIAPaCa-2 (pancreas) | 1.9 | 1.0 |
| HL60 (leukemia) | 4.1 | 3.7 |
| MCF7 (breast) | 5.2 | 9.1 |
| MDA-MB-231 (breast) | 4.3 | 6.2 |

[a]Cells were exposed for 96 hours and the number of viable cells was measured using the MTS reagent. $IC_{50}$ values were calculated as the concentration of compound eliciting a 50% inhibition of cell proliferation expressed in μM.

The biological results demonstrated that the compound (13) displayed promising in vitro anti-proliferative activity against various human cancer cell lines similar to that of CX-4945 used as reference drug.

Example 29

Evaluation of Inhibitory Activity on Protein Kinase CK2

CK2 Kinase Assay was conducted using the protocol as described in Pierre F. et al; *J. Med. Chem.* 2011, 54, 635-654. The tested compounds in aqueous solution were added at a volume of 10 μL to a reaction mixture comprising 10 μL of assay dilution buffer (ADB; 20 mM MOPS, pH 7.2, 25 mM β-glycerol phosphate, 5 mM EGTA, 1 mM sodium orthovanadate, and 1 mM dithiothreitol), 10 μL of substrate peptide (RRRDDDSDDD, dissolved in ADB at a concentration of 1 mM), 10 μL of recombinant human CK2 (RRββ-holoenzyme, 25 ng dissolved in ADB; Millipore). Reactions were initiated by the addition of 10 μL of ATP solution (90% 75 mMMgCl2, 75 μM ATP (final ATP concentration:15 μM) dissolved in ADB; 10% [γ-33P] ATP (stock 1mCi/100 μL; 3000 Ci/mmol (Perkin-Elmer) and maintained for 10 min at 30° C. The reactions were quenched with 100 μL of 0.75% phosphoric acid and then transferred to and filtered through a phosphor cellulose filter plate (Millipore). After washing each well five times with 0.75% phosphoric acid, the plate was dried under vacuum for 5 min and, following the addition of 15 μL of scintillation fluid to each well, the residual radioactivity was measured using a Wallac luminescence counter. The $IC_{50}$ values were derived from eight concentrations of test inhibitors.

The biological results demonstrated that the present compounds possessed favourable CK2 inhibition with $IC_{50}$ at a nanomolar concentration range.

By way of example, the compound (13) displayed promising protein kinase CK2 activity with an $IC_{50}$ of 83 nM, while in the same experimental condition, the reference control CX-4945 inhibited protein kinase CK2 activity of 1 nM.

It is to be understood that the 3-substituted amino-2-arylpyrrolo[2,3-c]pyridine derivatives are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A compound having the formula I:

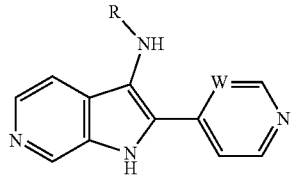

or a pharmaceutically acceptable salt or stereoisomer thereof,
wherein:
W is CH or N;
R is $(CH_2)_{2-3}NR_3R_4$, $CH_2Ar$, $C(O)$—$(CH_2)_{2-3}NR_3R_4$, $C(O)Ar$, $S(O)_2$—$(CH_2)_{2-3}NR_3R_4$, $S(O)_2Ar$, or Ar;
Ar is aryl or 5- or 6-membered heteroaryl, wherein the aryl or 5- or 6-membered heteroaryl is optionally substituted with one, two, or three substituents independently selected from the group consisting of halogen, CN, $C_1$-$C_6$ alkyl, $C_1$-$C_6$ haloalkyl, $C_1$-$C_6$ cyanoalkyl, $C(O)R_1$, $C(O)NR_1R_2$, $C(O)OR_1$, $NR_1R_2$, $NHC(O)R_1$, $NHC(O)NHR_1$, $NHC(O)OR_1$, $NHS(O)_2R_1$, $NHS(O)_2NHR_1$, $OR_1$, $S(O)_2NR_1R_2$, $C_3$-$C_6$ cycloalkyl, $C_3$-$C_6$ halocycloalkyl, and $C_3$-$C_6$ cyanocycloalkyl;
each $R_1$ is independently H, $C_1$-$C_6$ alkyl, $C_1$-$C_6$ haloalkyl, $C_1$-$C_6$ cyanoalkyl, $C_3$-$C_6$ cycloalkyl, $C_3$-$C_6$ halocycloalkyl, or $C_3$-$C_6$ cyanocycloalkyl;
each $R_2$ is independently H, $C_1$-$C_6$ alkyl, $C_1$-$C_6$ haloalkyl, $C_1$-$C_6$ cyanoalkyl, $C_3$-$C_6$ cycloalkyl, $C_3$-$C_6$ halocycloalkyl, or $C_3$-$C_6$ cyanocycloalkyl;
each $R_3$ is independently H, $C_1$-$C_6$ alkyl, $C_1$-$C_6$ haloalkyl, $C_1$-$C_6$ cyanoalkyl, $C_3$-$C_6$ cycloalkyl, $C_3$-$C_6$ halocycloalkyl, or $C_3$-$C_6$ cyanocycloalkyl; and
each $R_4$ is independently H, $C_1$-$C_6$ alkyl, $C_1$-$C_6$ haloalkyl, $C_1$-$C_6$ cyanoalkyl, $C_3$-$C_6$ cycloalkyl, $C_3$-$C_6$ halocycloalkyl, or $C_3$-$C_6$ cyanocycloalkyl; or
any $R_3$ and $R_4$, taken together with the nitrogen atom to which they are attached, independently forms a nitrogen-containing heterocyclyl, wherein each nitrogen-containing heterocyclyl is optionally and independently substituted with one, two, or three substituents independently selected from the group consisting of halogen, $C_1$-$C_6$ alkyl, $C_1$-$C_6$ trihaloalkyl, OH, and $OC_1$-$C_6$ alkyl.

2. The compound of claim 1, or a pharmaceutically acceptable salt or stereoisomer thereof, wherein R is $(CH_2)_2NR_3R_4$, $CH_2Ar$, $C(O)Ar$, or Ar, wherein the Ar of $CH_2Ar$, $C(O)Ar$, or Ar is optionally substituted with one, two, or three substituents independently selected from the group consisting of halogen, CN, $C_1$-$C_6$ alkyl, $C_1$-$C_6$ haloalkyl, $C_1$-$C_6$ cyanoalkyl, $C(O)R_1$, $C(O)NR_1R_2$, $C(O)OR_1$, $NR_1R_2$, $NHC(O)R_1$, $NHC(O)NHR_1$, $NHC(O)OR_1$, $NHS(O)_2R_1$, $NHS(O)_2NHR_1$, $OR_1$, $S(O)_2NR_1R_2$, $C_3$-$C_6$ cycloalkyl, $C_3$-$C_6$ halocycloalkyl, and $C_3$-$C_6$ cyanocycloalkyl.

3. The compound of claim 2, or a pharmaceutically acceptable salt or stereoisomer thereof, wherein:
R is $(CH_2)_2NR_3R_4$;
$R_3$ is $C_1$-$C_6$ alkyl; and
$R_4$ is $C_1$-$C_6$ alkyl.

4. The compound of claim 3, or a pharmaceutically acceptable salt or stereoisomer thereof, wherein:

$R_3$ is $CH_3$; and
$R_4$ is $CH_3$.

5. The compound of claim 2, or a pharmaceutically acceptable salt or stereoisomer thereof, wherein:
R is $CH_2Ar$; and
Ar is phenyl, wherein the phenyl is substituted with one Cl substituent.

6. The compound of claim 2, or a pharmaceutically acceptable salt or stereoisomer thereof, wherein:
R is $CH_2Ar$; and
Ar is pyridin-3-yl.

7. The compound of claim 2, or a pharmaceutically acceptable salt or stereoisomer thereof, wherein:
R is C(O)Ar; and
Ar is phenyl, wherein the phenyl is substituted with one substituent selected from the group consisting of Cl, $CH_3$, and $N(CH_3)_2$.

8. The compound of claim 2, or a pharmaceutically acceptable salt or stereoisomer thereof, wherein:
R is Ar; and
Ar is phenyl, wherein the phenyl is substituted with one, two, or three substituents independently selected from the group consisting of halogen, $C_1$-$C_6$ alkyl, C(O)$NR_1R_2$, and $NR_1R_2$.

9. The compound of claim 8, or a pharmaceutically acceptable salt or stereoisomer thereof, wherein Ar is phenyl, wherein the phenyl is substituted with one, two, or three substituents independently selected from the group consisting of Cl, $CH_3$, $CH(CH_3)_2$, $C(O)N(CH_3)_2$, and $N(CH_3)_2$.

10. The compound of claim 2, or a pharmaceutically acceptable salt or stereoisomer thereof, wherein:
R is Ar; and
Ar is pyridin-2-yl.

11. The compound of claim 1, wherein the compound is selected from the group consisting of:

(1)
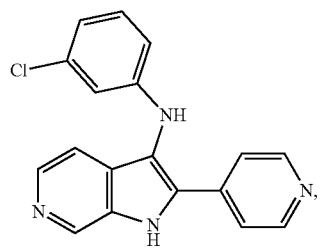

(2)
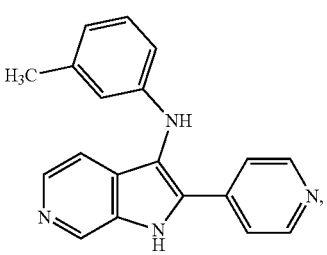

(3)
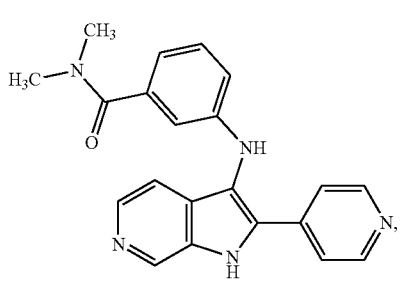

(4)
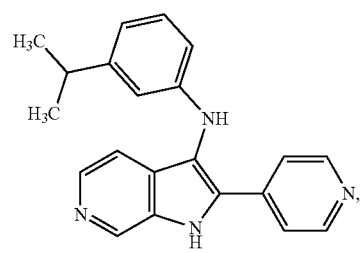

(5)
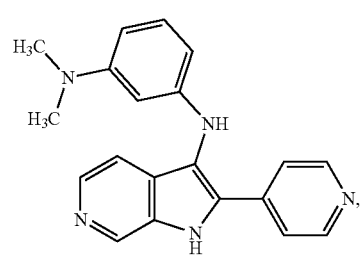

(6)
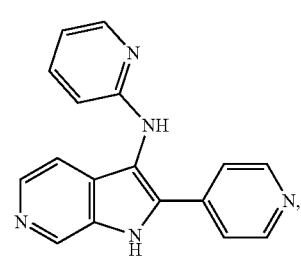

(7)
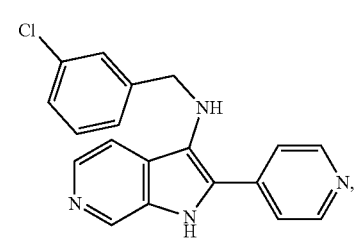

(8)
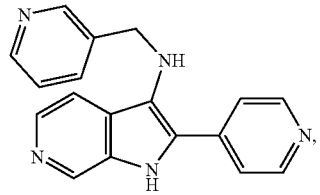

(9)
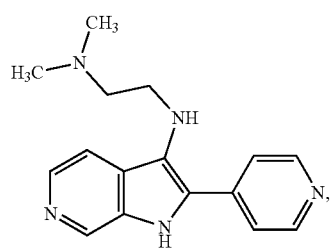

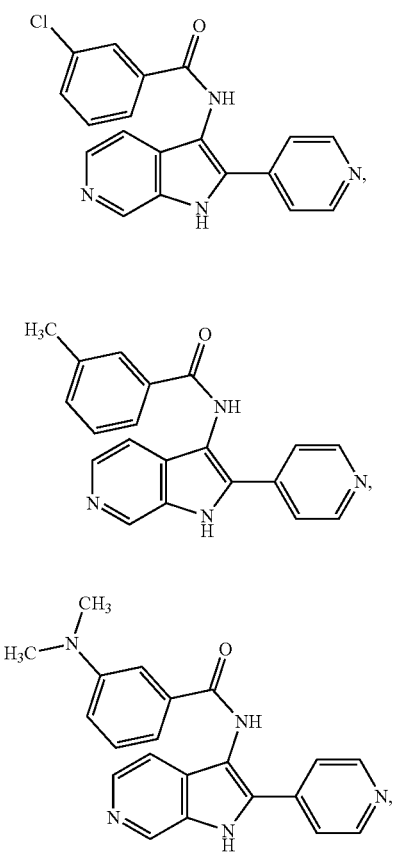
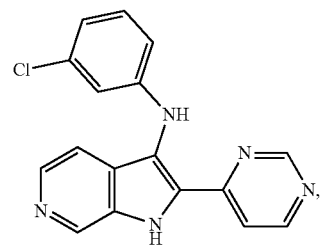
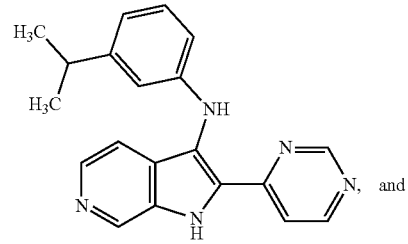
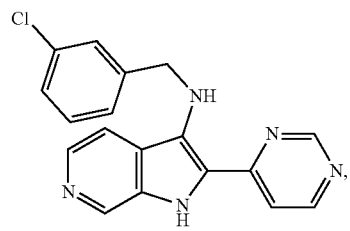
or a pharmaceutically acceptable salt thereof.
12. A pharmaceutical composition comprising a pharmaceutically acceptable carrier and a therapeutically effective amount of the compound of claim 1, or a pharmaceutically acceptable salt or stereoisomer thereof.
* * * * *